United States Patent
Zhou et al.

(10) Patent No.: US 10,055,827 B2
(45) Date of Patent: Aug. 21, 2018

(54) DIGITAL IMAGE FILTERS AND RELATED METHODS FOR IMAGE CONTRAST ENHANCEMENT

(75) Inventors: Chunhong Zhou, Oceanside, CA (US); Arup Roy, Valencia, CA (US); Kelly H. McClure, Simi Valley, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 981 days.

(21) Appl. No.: 12/560,581

(22) Filed: Sep. 16, 2009

(65) Prior Publication Data
US 2010/0067825 A1 Mar. 18, 2010

Related U.S. Application Data

(60) Provisional application No. 61/097,481, filed on Sep. 16, 2008.

(51) Int. Cl.
*G06K 9/00* (2006.01)
*G06T 5/40* (2006.01)
*G06T 5/00* (2006.01)
*A61N 1/36* (2006.01)

(52) U.S. Cl.
CPC ............... *G06T 5/40* (2013.01); *G06T 5/009* (2013.01); *A61N 1/36046* (2013.01); *G06T 2207/10016* (2013.01)

(58) Field of Classification Search
CPC .......................... A61N 1/36046; G06T 5/009
USPC .............. 382/128, 168, 254, 274; 607/53–54
See application file for complete search history.

(56) References Cited

U.S. PATENT DOCUMENTS

| | | | | |
|---|---|---|---|---|
| 4,573,070 A | * | 2/1986 | Cooper | 348/617 |
| 5,109,844 A | * | 5/1992 | de Juan et al. | 607/53 |
| 5,674,263 A | * | 10/1997 | Yamamoto et al. | 607/54 |
| 5,796,874 A | * | 8/1998 | Woolfe | G06T 5/007 358/509 |
| 5,862,254 A | * | 1/1999 | Kim et al. | 382/168 |
| 5,930,402 A | * | 7/1999 | Kim | 382/274 |
| 5,935,155 A | * | 8/1999 | Humayun et al. | 607/54 |
| 6,400,989 B1 | * | 6/2002 | Eckmiller | 607/54 |
| 6,458,157 B1 | * | 10/2002 | Suaning | 623/6.63 |
| 6,580,835 B1 | * | 6/2003 | Gallagher et al. | 382/274 |
| 6,873,742 B2 | * | 3/2005 | Schu | 382/274 |

(Continued)

FOREIGN PATENT DOCUMENTS

JP 10210324 A * 8/1998 .............. H04N 5/20

OTHER PUBLICATIONS

Tae Keun Kim; Joon Ki Paik; Bong Soon Kang; , "Contrast enhancement system using spatially adaptive histogram equalization with temporal filtering," Consumer Electronics, IEEE Transactions on , vol. 44, No. 1, pp. 82-87, Feb. 1998.*

(Continued)

*Primary Examiner* — Gandhi Thirugnanam
(74) *Attorney, Agent, or Firm* — Scott Dunbar

(57) ABSTRACT

Digital image filters and related methods for image contrast enhancement are disclosed. According to one aspect of the method, an invariant brightness level is initially determined. For each pixel of an input image, the invariant brightness level is subtracted from the input brightness of the pixel. The resulting value is multiplied with a contrast adjustment constant. After that, the invariant brightness level is added. Further aspects of the method can involve histogram equalization.

9 Claims, 5 Drawing Sheets

(56) References Cited

U.S. PATENT DOCUMENTS

| | | | |
|---|---|---|---|
| 6,920,358 B2* | 7/2005 | Greenberg et al. | 607/54 |
| 7,266,413 B2* | 9/2007 | Greenberg et al. | 607/54 |
| 7,424,148 B2* | 9/2008 | Goh | 382/169 |
| 7,457,434 B2* | 11/2008 | Azar | 382/103 |
| 7,668,599 B2* | 2/2010 | Greenberg et al. | 607/54 |
| 7,755,598 B2* | 7/2010 | Yang et al. | 345/102 |
| 7,925,354 B2* | 4/2011 | Greenberg et al. | 607/54 |
| 8,000,554 B2* | 8/2011 | Li et al. | 382/274 |
| 8,019,428 B2* | 9/2011 | Greenberg et al. | 607/54 |
| 8,160,383 B2* | 4/2012 | Manabe | 382/274 |
| 8,417,032 B2* | 4/2013 | Mizuno et al. | 382/168 |
| 8,428,741 B2* | 4/2013 | Greenberg et al. | 607/54 |
| 8,606,037 B2* | 12/2013 | Ali | 382/274 |
| 2002/0010496 A1* | 1/2002 | Greenberg et al. | 607/54 |
| 2002/0136464 A1* | 9/2002 | Schu | 382/274 |
| 2003/0161549 A1* | 8/2003 | Lei et al. | 382/274 |
| 2005/0036071 A1* | 2/2005 | Kim | 348/678 |
| 2005/0104974 A1* | 5/2005 | Watanabe | H04N 1/6027 348/222.1 |
| 2005/0288735 A1* | 12/2005 | Greenberg et al. | 607/54 |
| 2006/0013503 A1* | 1/2006 | Kim | G06T 5/009 382/276 |
| 2006/0106432 A1* | 5/2006 | Sawan et al. | 607/54 |
| 2006/0147105 A1* | 7/2006 | Lee et al. | 382/151 |
| 2007/0024638 A1* | 2/2007 | Hoppe et al. | 345/606 |
| 2007/0171310 A1* | 7/2007 | Arici et al. | 348/687 |
| 2007/0216813 A1* | 9/2007 | Arici et al. | 348/630 |
| 2007/0299484 A1* | 12/2007 | Greenberg et al. | 607/54 |
| 2008/0021516 A1* | 1/2008 | Greenberg et al. | 607/54 |
| 2009/0268973 A1* | 10/2009 | Majewicz | G06T 5/40 382/237 |
| 2010/0036457 A1* | 2/2010 | Sarpeshkar et al. | 607/53 |
| 2010/0067825 A1* | 3/2010 | Zhou et al. | 382/274 |
| 2011/0181787 A1* | 7/2011 | Wang et al. | 348/673 |
| 2011/0288612 A1* | 11/2011 | Greenberg et al. | 607/54 |
| 2012/0002890 A1* | 1/2012 | Mathew | H04N 5/23267 382/232 |

OTHER PUBLICATIONS

Wentai Liu et al., "Image Processing and Interface for retinal Visual Prostheses", 2005, IEEE International Symposium on Circuits and Systems, p. 2927-2930.*

Takasugi, Hiroshi, JP 10210324 Image Processing Unit(English Translation), 1998, p. 1-11.*

Arici, T. et al, "Image Local Contrast Enhancement Using Adaptive Non-Linear Filters", 2006, IEEE International Conference on Image Processing 2006, p. 1-9.*

"Digital Image Enhancement and Noise Filitering by Use of Local Statistics", J. Lee, IEEE Transactions on Pattern Analysis and Machine Intelligence. vol. PAMI-2, No. 2, Mar. 1980; pp. 165-168.

"Natural Scenes Classification for Color Enhancement", F. Naccari, S. Battiato, A. Bruna, A. Capra, and A. Castorina, IEEE Transactions on Computer Electronics. vol. 51, No. 1, Feb. 2005; pp. 234-239.

"A Fast and Adaptive Mehtod for Image Contrast Enhancement", Z. Yu and C. Bajaj, Department of Computer Sciences, University of Texas at Austin, Austin, TX 78712-1188 USA; 2004 International Conference on Image Processing (ICIP). vol. 2, Oct. 2004; pp. 1001-1004.

"Contrast Stretching", R. Fisher, S. Perkins, A. Walker, and E. Wolfart, http://homepages.inf.ed.ac.uk/rbf/HIPR2/stretch.htm, 2003; pp. 1-5.

"Single-Chip CMOS Image Sensors for a Retina Implant System", M. Schwarz, R. Hauschild, B. Hosticka, J. Huppertz, T. Kneip, S. Kolnsberg, L. Ewe, and H. K. Trieu, IEEE Transactions on Circuits and Systems—II: Analog and Digital Signal Processing. vol. 46, No. 7. Jul. 1999; pp. 870-876.

* cited by examiner

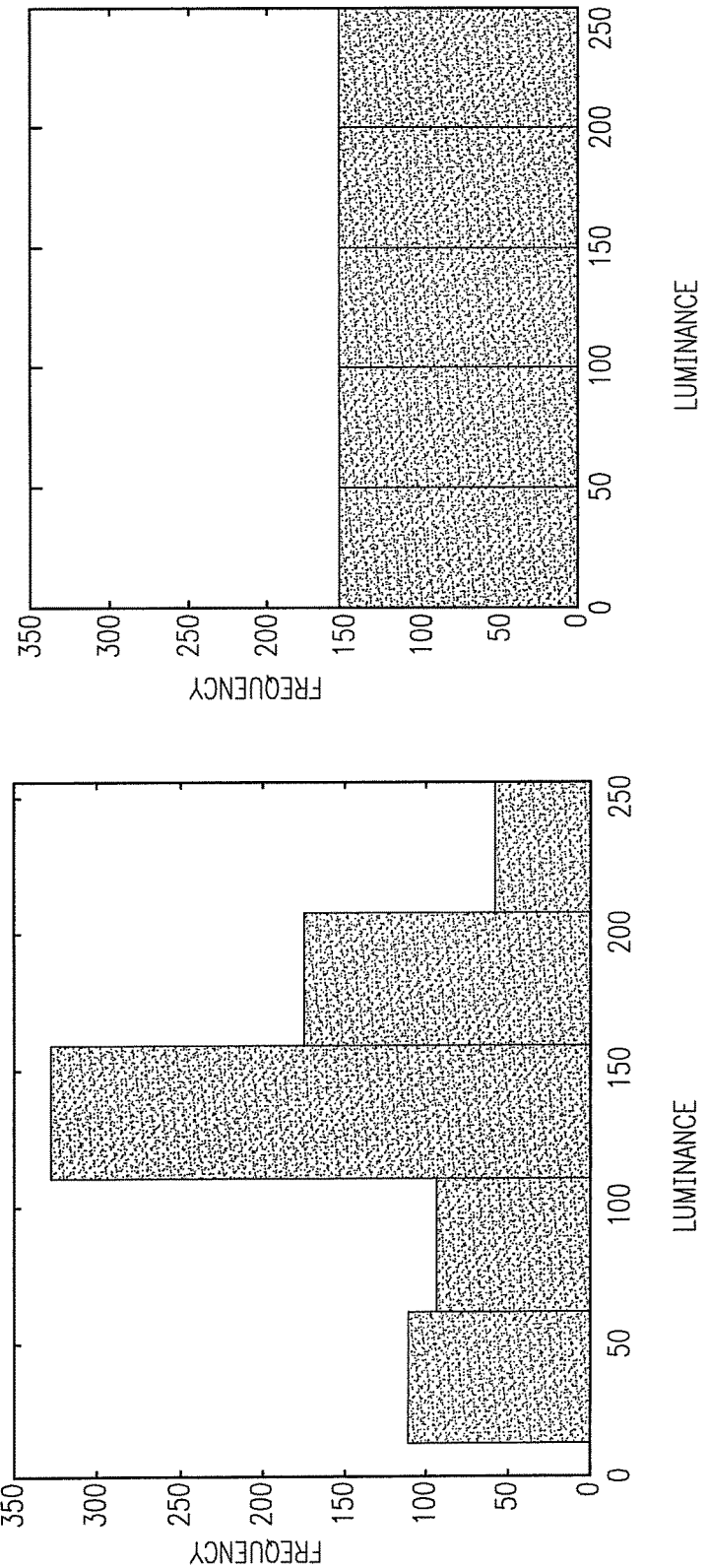

DIGITAL IMAGE FILTERS AND RELATED METHODS FOR IMAGE CONTRAST ENHANCEMENT

CROSS REFERENCE TO RELATED APPLICATIONS

The present application claims priority to U.S. Provisional Application No. 61/097,481 filed on Sep. 16, 2008 and incorporated herein by reference in its entirety.

FIELD

The present disclosure relates to digital image filters. More in particular, it relates to digital image filters and related methods for image contrast enhancement.

SUMMARY

According to a first aspect, a method for image contrast enhancement of a digital image comprising a plurality of pixels is provided, each pixel having an input brightness, the method comprising: determining an invariant brightness level; for each pixel, subtracting the invariant brightness level from the input brightness of the pixel, thus obtaining a first intermediate brightness value for the pixel; for each pixel, multiplying the first intermediate brightness value with a contrast adjustment constant, thus obtaining a second intermediate brightness value for the pixel; and for each pixel, adding the invariant brightness level to the second intermediate brightness value, thus obtaining an output brightness value for that pixel.

According to a second aspect, an image contrast enhancement filter to filter an input digital image and produce an output digital image is provided, the filter processing each pixel of the input digital image through a transfer function $I_{out}=(I_{in}-L)C+L$, wherein $I_{in}$ is the input pixel brightness, $I_{out}$ is the output pixel brightness, C is a contrast adjustment constant, and L is an invariant brightness level.

According to a third aspect, a visual prosthesis comprising an image contrast enhancement filter is disclosed. The image contrast enhancement filter can be based on image histogram equalization, so that the an output image output by the image contrast enhancement filter has an output image histogram which is an equalized version of the input image histogram.

Further embodiments are shown in the written specification, drawings and claims of the present application.

BRIEF DESCRIPTION OF THE FIGURES

FIGS. 5A and 5B shows a further embodiment of the present disclosure implementing histogram equalization. The cluster of luminances around mid-gray in FIG. 5A is redistributed more evenly across the entire range in FIG. 5B.

DETAILED DESCRIPTION

The present disclosure provides digital image filters and related methods for image contrast enhancement, especially in the field of visual prosthetic devices.

According to an embodiment of the present disclosure, the digital image filters and related methods for image contrast enhancement are based on detecting an invariant brightness level and stretching the image histogram. An invariant brightness level (L) is defined as the brightness level which does not change before and after the contrast enhancement process. The histogram stretching can be done by multiplying image pixel values with a contrast setting C.

Figure 1:
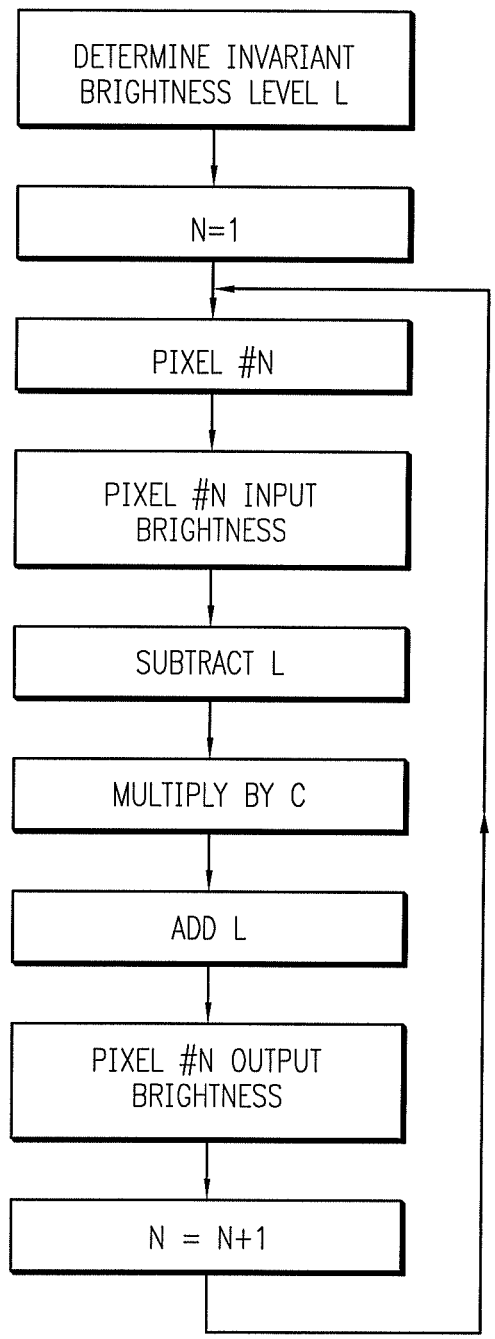
FIG. 1 shows a flow chart of an embodiment of the present disclosure in accordance with expression (1) below.

This process can be formulated as:

$$I_{out}=(I_{in}-L)C+L \qquad (1)$$

in which $I_{in}$ is the input brightness, $I_{out}$ is the output pixel brightness, C is the contrast adjustment constant and L is the invariant brightness level. In other words, the following four operations are performed: 1) determining an invariant brightness level (L); 2) for each pixel, subtracting such invariant brightness level (L) from the input brightness ($I_{in}$) of the pixel; 3) multiplying the resulting brightness with a contrast setting (C); and 4) adding the brightness level (L) to such multiplied value. FIG. 1 shows a flow chart of this method.

Using the above transformation (1), if $I_{in}$=L, the output will be $I_{out}$=L. This states that an input pixel of brightness L does not change its brightness level after the contrast enhancement. However, pixels brighter than L will be brighter (because $I_{in}$-L>0), while darker pixels will be darker (because $I_{in}$-L<0). In addition, the more different $I_{in}$ is from L, the more $I_{in}$ will be enhanced by the multiplication process.

The main difference between the method according to the present disclosure and the known contrast enhancement method through multiplication is the presence of the invariant level L, which helps to keep a certain brightness level invariant before and after the enhancement process.

Many methods can be used to detect the invariant brightness level L. A first method is that of finding the darkest pixel in the scene, so that a dark object will be kept dark after the transformation. Other brighter pixels, in this method, will be enhanced and become brighter.

In this way, the overall contrast of the images is enhanced without artificially increasing the brightness level of the dark objects.

Alternatively, instead of picking the darkest pixel, L can be determined by finding the $N^{th}$ darkest pixel where N is a small number, so that the choice is less affected by image noise. Such filter parameter N can be determined empirically. For example, N can be defined as the $10^{th}$ percentile of the pixels in a scene. If such formula is applied to a completely dark image (where, e.g., 90% of the pixels have a 10 value while the remaining 10% of the pixels have a 12 value on a scale 0-255), since L is determined going up on the histogram and the brightness values are discrete, the algorithm will use L=10. Such result is interesting, because it means that 90% of the pixels have a brightness less than or equal to 10. This is where the method according to the present disclosure will help reduce the noise artifacts in a completely dark image.

In other words, assuming that the camera generating the digital image is pointed at an uniformly bright scene, the L chosen according to the above method will be very close to the actual brightness level (not identical due to possible noisy pixels in the scene). As a consequence, the output pixels will all be very close to their original brightness level, even when enhanced by the multiplying factor C, since the variations from L are very small.

Figure 2:
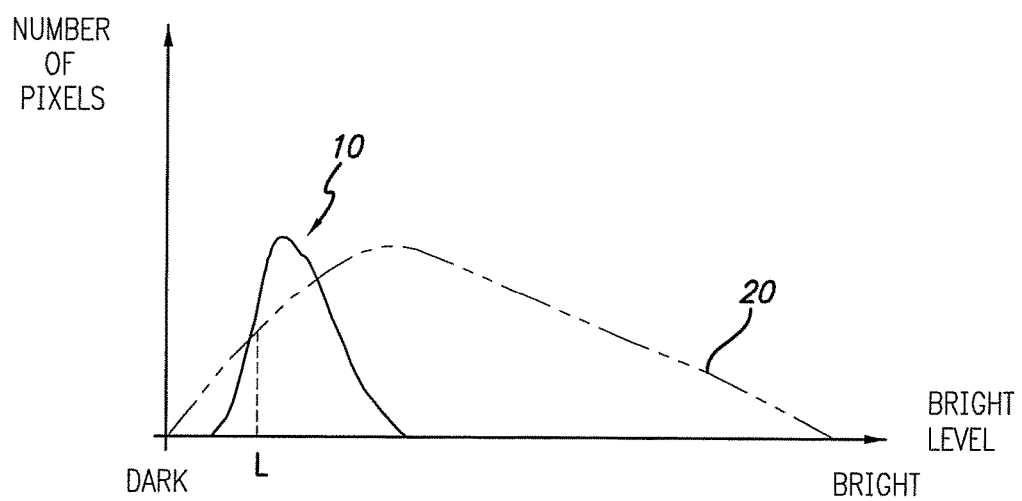
FIG. 2 shows a comparative diagram of histograms before and after the filtering of the present disclosure.

The following FIG. 2 shows an example of the input image histogram (10) and output image histogram (20) of the method according to the present disclosure, where the invariant level L is determined using the method mentioned above, i.e. by choosing one of the darkest pixels of the input image. FIG. 2 explains the method according to the present disclosure, i.e. detecting L and converting an input image histogram to an output image histogram. Therefore, starting with the solid line input histogram (10), L is found based on such histogram, and then the above formula is used to compute the output. The output image will have the histogram (20) shown in the dashed line.

As also mentioned above, L can be chosen in different ways. Ideally, L represents what a dark object will look like in the image. Therefore, image segmentation of the scene can be performed and an average brightness be calculated for each of the objects. Once this is done, the darkest among the average brightness values can be used as L.

The contrast adjustment constant C can be either fixed, or determined based on the scene information. If C is fixed, it can be determined empirically by going through a collection of representative images pertaining to the environment for which the filter is designed. If, on the other hand, C is based on scene information, the more objects there are in the image, the more likely the use of a high contrast gain setting C. There are many ways to determine the amount of objects in the presence of image noise. For example, a contour detection technique will find more contour pixels in an image with more objects. Thus, C can be determined as an increasing function of the number of contour pixels.

The method according to the present disclosure is easy to implement, easy to verify and takes very little time to run. In particular, according to one of the embodiments of the present disclosure, a standard histogram is built for every frame. Then L is computed by counting an N number of pixels starting from the darkest pixel value. A preset C is used for enhancement. All these operations are deterministic in nature. The total run time will be O(n) with two passes of each image frame.

The method according to the present disclosure can be used in combination with other filters. In particular, it should be noted that the output of the filter is in the same image domain as the input, i.e. it is of the same size and depth. Therefore, it can be stacked up with other processing methods.

Figure 3:
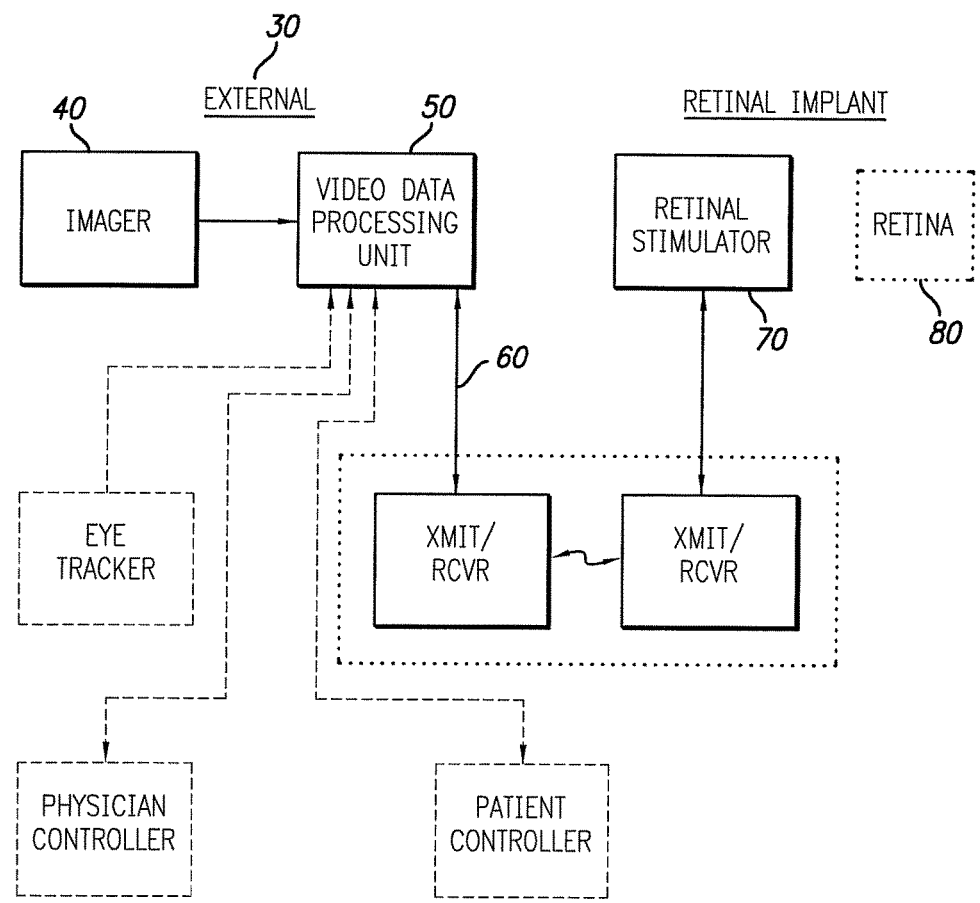
FIG. 3 shows a schematic representation of the main components of a visual prosthesis.
Figure 6:
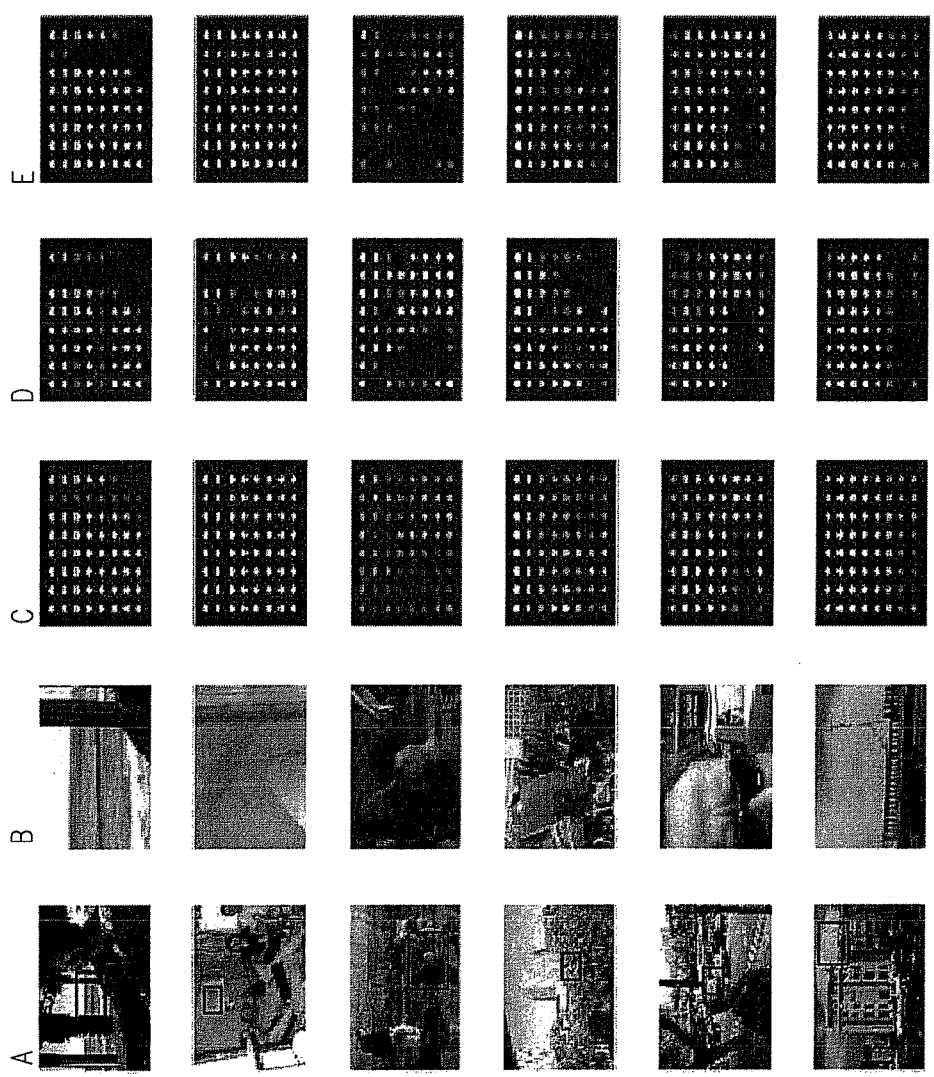
FIGS. 6A-6E show examples of images where histogram equalization has been implemented.

In particular, FIG. 3 shows a schematic representation of the main components of a visual prosthesis taken from U.S. published patent application 2005/0288735, incorporated herein by reference in its entirety. In particular, the external portion (30) of the visual prosthesis comprises an imager (40), e.g., a video camera to capture video in real time, and a video data processing unit (50) comprising a Digital Signal Processor (DSP) to process video data and then send output commands (60) for a retinal stimulator (70) to be implanted on the retina (80) of a patient. The filter and filtering method according to the present disclosure can be contained in the DSP of the video data processing unit (50).

Figure 4:
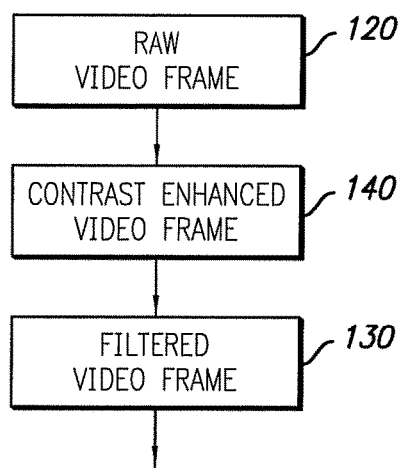
FIG. 4 schematically shows a possible location of the filter in accordance with the disclosure.

FIG. 4 shows a possible structure of the video data processing unit (50), which comprises a video input handler (120) to acquire a raw video input and a video filter processor (130), the latter performing filtering to produce a video output image, e.g. a 6×10 image, that can be used by a telemetry engine. As shown in FIG. 4, the filter (140) according to the present disclosure can be located between the video input handler (120) and the video filter processor (130).

However, use in a visual prosthesis is just one of the applications of the filter and method according to the disclosure. In particular, it can be used in any video-based medical devices.

The method according to the present disclosure can work under a variety of lighting conditions, in particular low-light and low-contrast environments.

A further embodiment of the present disclosure allows the contrast to be changed in accordance with this equation:

$$Pout=(Pin-AvgBr)C+AvgBr$$

where C=Contrast Level
AvgBr=Average luminance Value
Pin=Pixel value of input image
Pout=Pixel value of output image In other words, the invariant brightness level L of equation (1) is chosen to be the average luminance value of the image.

Another embodiment of the present disclosure adopts a contrast scaling (normalization) algorithm that sets a linear scaling function to utilize the full brightness range of the camera.

$$Pout=((Pin-c)/(d-c))\times(\text{brightness range})+\text{minimum camera brightness}$$

Where 'd' can be maximum intensity value from the input image intensity histogram or the 95th percentile etc, 'c' can be the minimum intensity value from the input image intensity histogram or the 5th percentile etc, and the brightness range could be either the full range (0 to 255 for a grey scaled image) or a specified subset of that depending on the minimum camera brightness.

According to a further embodiment of the present disclosure, another method to systematically increasing small differences in luminance can be via histogram equalization. This embodiment can use a non-linear monotonic scaling function to make the brightness distribution function (the probability distribution of the luminance values) of the filtered image to follow a uniform density function (luminance values are distributed more evenly). Filtering in the time domain can also be incorporated in a similar fashion as mentioned above.

Each of the above discussed methods can be made settable by a personal computer, be applied automatically on every video frame or can be made adaptive depending on the luminance distribution of the images at any instant of time.

If desired, the method can incorporate the luminance "history" (a record of the luminance ranges) over several video frames.

Subjects cannot distinguish fine brightness differences (when asked to identify or rate brightness they can only reliably distinguish about 5 levels of brightness), so small differences in luminance will be imperceptible. A method of systematically increasing small differences in luminance can be performed via histogram equalization.

Reference will now be made to FIG. 5. Panel A shows the actual frequency histogram for the electrode outputs (based on the unsealed mean) of luminances found in one scene, it can be seen that midrange gray luminances are very common, and light and dark values are relatively infrequent. Panel B shows an example of a desired histogram, where electrode outputs can take 5 possible luminances, and the luminances are distributed more evenly across the range of luminance values. Examples of histogram equalization are shown in FIGS. 6A-6E. The full scene is shown in Panel A, and a scaled image patch is shown in Panel B. Panel C shows electrode output based on a scaled mean. Panel D shows electrode output based on local histogram equalization within the image patch.

Histogram equalization involves ordering each scaled mean electrode output in terms of its luminance value, and then reassigning it a luminance based on the new histogram—so the darkest ⅕th of electrodes will be assigned a luminance of 25, the second darkest ⅕th of electrodes will be assigned a luminance of 75, and so on. Note that this histogram does not permit small differences in luminance. In Panel D where histogram equalization is carried out locally for each single image patch we see some problems (e.g. the second row) with over-scaling as a consequence of the histogram equalization being carried out over a small number of data points. As a result essentially identical luminance values can end up being assigned very different luminance values. To avoid these problems with inappropriate scaling histogram equalization should be carried out globally using either the entire field of view of the camera, and/or based on "history" over several seconds (as with second-stage luminance scaling see above). Examples of global histogram equalization scaling are shown in Panel E of FIG. 6.

It should be noted that histogram equalization should be carried out subsequent to the sub-setting for each electrode, and that, like second-stage luminance scaling, it will override the effects of first-stage luminance scaling.

In summary, histogram equalization may provide further benefits beyond those of simple second stage luminance scaling. In view of the small field of view of the image, at this stage normalization should be based on a temporal average over several seconds and as wide a field of view as possible.

Accordingly, what has been shown are digital image filters and related methods for image contrast enhancement. While these filters and methods have been described by means of specific embodiments and applications thereof, it is understood that numerous modifications and variations could be made thereto by those skilled in the art without departing from the spirit and scope of the disclosure. It is therefore to be understood that within the scope of the claims, the disclosure may be practiced otherwise than as specifically described herein.

The invention claimed is:

1. A visual prosthesis comprising:
a video input device for providing video data;
a video processing unit, including a digital signal processor, receiving the video data from the video input device and converting the video data into a video output image, including an array of pixels, the video processing unit including:
an image contrast enhancement filter based on an invariant brightness level, and the formula Iout= (Iin−L) C+L, where Iout is output intensity, Iin is input intensity, L is the invariant brightness level, and C is a predetermined multiplier, and each pixel's difference from the invariant brightness level, where L is determined by segmentating the image to find objects, calculating an average brightness for each object, and setting L to be the darkest average brightness;
a video filter processor producing the video output image;
a telemetry engine transmitting the video output image; and
a neural stimulation system suitable to receive the video output image and to stimulate visual percepts according to the video output image.

2. The visual prosthesis of claim 1, wherein the image contrast enhancement filter is based on image histogram equalization, so that an output image output by the image contrast enhancement filter has an output image histogram which is an equalized version of the input image histogram.

3. The visual prosthesis of claim 2, wherein image histogram equalization operates through a nonlinear monotonic scaling function.

4. The visual prosthesis of claim 2, wherein the image contrast enhancement filter operates in the time domain.

5. The visual prosthesis of claim 1, wherein filtering through the contrast enhancement filter is automatically set.

6. The visual prosthesis of claim 2, wherein filtering through the contrast enhancement filter is applied automatically on every video frame of the video data.

7. The visual prosthesis of claim 2, wherein filtering through the contrast enhancement filter is an adaptive filtering.

8. The visual prosthesis of claim 7, wherein the adaptive filtering depends on a luminance distribution of input images at any instant of time.

9. The visual prosthesis of claim 2, wherein the image histogram equalization is based on a temporal average.

* * * * *